United States Patent [19]

Cook et al.

[11] 4,020,077
[45] Apr. 26, 1977

[54] ANTIBIOTICS

[75] Inventors: Martin Christopher Cook, Chalfont St. Peter; Brian Laundon, Northolt, all of England

[73] Assignee: Glaxo Laboratories Limited, Greenford, England

[22] Filed: May 21, 1976

[21] Appl. No.: 688,778

Related U.S. Application Data

[62] Division of Ser. No. 377,247, July 9, 1973, Pat. No. 3,974,150.

[30] Foreign Application Priority Data

July 21, 1972 United Kingdom ............. 34298/72

[52] U.S. Cl. ..................... 260/306.7 C; 260/239.1
[51] Int. Cl.$^2$ ..................................... C07D 499/02
[58] Field of Search .................. 260/239.1, 306.7 C

[56] References Cited

UNITED STATES PATENTS 3,763,154  10/1973  Henniger ..................... 260/243 C

*Primary Examiner*—Gerald A. Schwartz
*Attorney, Agent, or Firm*—Bacon & Thomas

[57] ABSTRACT

Novel 6$\beta$-isocyano penicillin and 7$\beta$-isocyano cephalosporin esters of value as intermediates in the synthesis of penicillin and cephalosporin antibiotics are provided. The novel compounds may be prepared by reaction of the corresponding 6$\beta$-formamido penicillin ester or 7$\beta$-formamido cephalosporin ester with an acid halide derived from phosphorus, sulphur or carbon or from an oxygen acid of one of said elements, suitable halides including thionyl chloride or phosgene, or with a trivalent phosphorus compound such as triphenylphosphine and a halogenated hydrocarbon such as carbon tetrachloride. The conversion of the novel products to 6$\beta$- and 7$\beta$-($\alpha$-hydroxy) arylacetamido penicillins and cephalosporins respectively by reaction under acidic conditions with an aromatic aldehyde followed by treatment with an aqueous medium is also described.

3 Claims, No Drawings

ANTIBIOTICS

This is a division of application Ser. No. 377,247, filed July 9, 1973, now U.S. Pat. No. 3,974,150.

This invention is concerned with improvements in or relating to the preparation of antibiotics. More particularly the invention is concerned with a novel group of β-lactam compounds of use as intermediates in the preparation of β-lactam antibiotics.

The cephalosporin compounds referred to in this specification are generally named with reference to cepham (*J. Amer. Chem. Soc.* 1962, 84, 3400). The term "cephem" refers to the basic cepham structure with one double bond. The penicillin compounds referred to in the specification are generally named with reference to penam (*J. Amer. Chem. Soc.* 1953, 75, 3293).

In the synthesis of antibiotics of the cephalosporin and penicillin type it is frequently required to modify the 6- or 7-acylamido side chain present in, for example, naturally occurring fermentation produced penicillins and cephalosporins respectively in order to obtain compounds with enhanced antibiotic activity. A commonly used method is deacylation to remove, for example, naturally occurring groups such as phenylacetyl or phenoxyacetyl, yielding a 6-aminopenicillanic acid or 7-aminocephalosporanic acid derivative, followed by N-acylation to introduce the desired 6- or 7-acyl group. One disadvantage of this method, however, is that is may not be possible or it may be difficult to prepare a stable acylating agent corresponding to the acyl group required to be introduced, so that a somewhat complex series of reactions may be necessary to introduce such N-acyl groups.

The present invention provides a novel group of β-lactam compounds of the penicillin and cephalosporin series the compounds being characterised by the presence of an isocyano group at the 6- or 7-position respectively. Such compounds are valuable intermediates in the synthesis of, for example, N-acylated penicillin and cephalosporin antibiotics by virtue of the reactive properties of the isocyano group.

Thus according to one feature of the invention we provide compounds of the general formula:

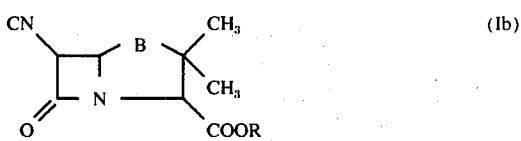

wherein R is a carboxyl blocking group. B is > S or > S → O (R or S) and Z represents a group in which 1 or 2 carbon atoms link the nuclear sulphur atom and the carbon atom carrying the blocked carboxyl group.

Important compounds of general formula I include cephalosporin compounds of the general formula:

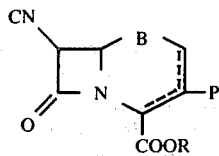

wherein R and B have the above-defined meanings, P is an organic group and the dotted line indicates that the compound maybe a ceph-2-em or ceph-3-em derivative. Examples of such compounds include deiphenylmethyl (6R, 7R)-7-isocyano-3-methylceph-3-em-4-carboxylate, diphenylmethyl (6R, 7R and S)-7-isocyano-3-acetoxymethylceph-3-em-4-carboxylate, and diphenylmethyl (6R,7R and S)-7-isocyano-3-(5-methyl-1,3,4-thiadiazol-2-ylthiomethyl)ceph-3-em-4-carboxylate, and diphenylmethyl (6R,7R)-7-isocyano-3-(1-methyltetrazol-5-ylthiomethyl)ceph-3-em-4-carboxylate.

Further important compounds of general formula I are penicillin compounds of general formula:

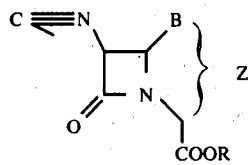

wherein R and B have the above-defined meanings. An example of such a compound is p-nitrobenzyl (3S,5R,6R and S)-6-isocyano-2,2-dimethylpenam-3-carboxylate.

It should be appreciated that formulae Ia and Ib are skeletal formulae and include within their scope compounds not specifically embraced therein structurally, for example 2-acetoxymethyl penicillins, 2-methyl and 2-methylene cephalosporins, 6α-methoxy penicillins and 7α-methoxy cephalosporins.

In the above formulae Ia and Ib, B is preferably > S.

The carboxyl blocking group R is advantageously an easily removable group formed by reaction of the carboxyl group with an aliphatic or araliphatic alcohol or a phenol, silanol, stannanol or acid, so that the group may be removed after subsequent transformation of the isocyano group to yield a penicillin or cephalosporin acid. We have found it generally undesirable to cleave the group R before transformation of the isocyano group since the cleavage reaction may promote decomposition, e.g. by hydrolysis or reduction, of the isocyano group and since the isocyano group may also be unstable in the presence of a free carboxy group.

Where the group —COOR is an ester group formed with an alcohol, phenol, silanol or stannanol the group R preferably has 1–20 carbon atoms. Suitable ester groups thus include those given in the following list, which is not intended to be an exhaustive list of possible ester groups.

i. — $COOCR^b R^c R^d$ wherein at least one of $R^b$, $R^c$ and $R^d$ is an electron-donor e.g. p-methoxyphenyl, 2,4,6-trimethylphenyl, 9-anthryl, methoxy, acetoxy, or fur-2-yl. The remaining $R^b$, $R^c$ and $R^d$ groups may be hydrogen or organic substituting groups. Suitable ester groups of this type include p-methoxybenzyloxycarbonyl and 2,4,6-trimethylbenzyloxy carbonyl.

ii. — $COOCR^b R^c R^d$ wherein at least one of $R^b$, $R_c$ and $R_d$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^b$, $R^c$, and $R_d$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. — COOCR$^b$R$^c$R$_d$ wherein at least two of R$^b$, R$^c$ and R$^d$ are hydrocarbon such as alkyl e.g. methyl or ethyl, or aryl e.g. phenyl and the remaining R$^b$, R$^c$ and R$^d$ group, if there is one, is hydrogen. Suitable esters of this type include t-butyloxycarbonyl, t-amyloxycarbonyl, diphenylmethoxycarbonyl and triphenylmethoxycarbonyl.

iv. — COOR$^e$ wherein R$^e$ is adamantyl, 2-benzyloxyphenyl, 4-methylthiophenyl, tetrahydrofur-2-yl or tetrahydropyran-2-yl.

v. Silyloxycarbonyl groups obtained by reaction of a carboxyl group with a derivative of a silanol. The derivative of a silanol is conveniently a halosilane or a silazane of the formula R$^4_3$SiX; R$^4_2$SiX$_2$; R$^4_3$Si.NR$^4_2$; R$^4_3$Si.NH.SiR$^4_3$; R$^4_3$Si.NH.COR$^4$; R$^4_3$Si.NH.CO.NH.SiR$^4_3$; R$^4$NH.CO.NR$^4$.SiR$^4_3$; or R$^4$C(OSiR$^4_3$): NSiR$^4_3$ where X is a halogen and the various groups R$^4$ which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as, for example, trimethylchlorosilane and dimethyldichlorosilane.

As indicated above, the group R may also be derived from an acid, and in such cases the group -COOR may be either a mixed or a symmetrical anhydride grouping.

According to a further feature of the invention we provide a process for the preparation of compounds of general formula I as hereinbefore defined which comprises reacting a compound of the general formula:

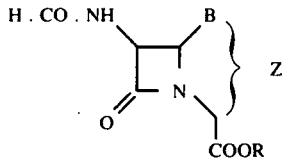

(where R, B and Z have the above defined meanings) with an acid halide derived frm phosphorus, sulphur or carbon or from an oxygen acid of one of said elements.

Acid halides which may be used in this process include phosphorus derivatives such as the trihalides and pentahalides, e.g. phosphorus trichloride, phosphorus tribromide and phosphorus pentachloride; derivatives of phosphorus oxyacids, e.g. phosphoryl chloride or bromide; derivatives of sulphur oxyacids, e.g. thionyl chloride; and derivatives of carbon oxyacids, e.g. phosgene and oxalyl chloride. It is particularly convenient to use acid halides such as thionyl chloride or phosgene which yield volatile by-products since this may facilitate subsequent separation and purification of the compound of formula I.

The process is preferably carried out in the presence of an inorganic base or a tertiary organic nitrogen base, and an inert solvent. The base, which serves to bind hydrogen halide produced in the course of the reaction and also prevents undesirable isomerisations, may be, for example, an inorganic base such as calcium carbonate or sodium bicarbonate or, more preferably, a tertiary organic base such as pyridine, N,N-dimethylaniline or triethylamine. The base may conveniently be used in quantities ranging from an approximate stoichiometric equivalent to about a 20-fold excess and in certain cases, e.g. where the base is pyridine, may also serve as the solvent. Alternatively, the reaction may be carried out in the presence of a cyclic ether, particularly a 1,2-lower alkylene oxide, e.g. a C$_{1-6}$ 1,2-lower alkylene oxide such as ethylene oxide or propylene oxide, in place of the base to remove the hydrogen halide. The alkylene oxide may similarly be used in quantities ranging from an approximate stoichiometric equivalent to about a 20-fold excess or may, if desired, serve as the solvent.

Where an inert solvent is used this may be any convenient aprotic solvent, for example, a chlorinated hydrocarbon such as methylene chloride or carbon tetrachoride, an aliphatic or cyclic ether such as diethyl ether, dioxan or tetrahydrofuran, a lower nitrile such as acetonitrile, an N,N-disubstituted amide such as dimethylformamide or dimethylacetamide, a hydrocarbon such as benzene or xylene or an ester such as ethyl acetate.

The reaction may conveniently be carried out at a temperature in the range $-100°$ C to $+100°$ C, advantageously $-80°$ C to $+20°$ C, preferably at about $-20°$ C. The course of the reaction may conveniently be monitored using thin layer chromatography.

The compounds of general formula I may also be prepared by reacting a compound of general formula II as hereinbefore defined with a trivalent phosphorus compound such as triphenyl phosphine and a halogenated hydrocarbon, preferably a carbon tetrahalide, e.g. carbon tetrachloride. The reaction is preferably carried out in the presence of a base, e.g. a tertiary amine such as pyridine or N,N-dimethylaniline although where a trivalent phosphorus compound such as triphenyl phosphine is used this may, if desired, also serve as the base.

Where the carboxyl blocking group is derived from an acid, a mixed carboxylic acid anhydride of formula II may, for example, be prepared by reacting under substantially anhydrous conditions a salt of the free acid corresponding to the compound of formula II with an acid halide such as a C$_1$ - C$_7$ acyl chloride, e.g. acetyl chloride, propionyl chloride or chloroacetyl chloride, advantageously in an inert solvent such as a halogenated hydrocarbon in the presence of a base such as a tertiary amine, for example as described in Belgian Pat. No. 780510. Symmetrical anhydrides of formula II may similarly be prepared as described in the said Belgian Patent by adding a halogenating agent such as phosphorus pentachoride to the free acid corresponding to formula II whereby about half the compound is converted to the corresponding acyl halide, which then reacts with the remaining free acid to yield the symmetrical anhydride. Similar reaction conditions to those used for the preparation of mixed anhydrides may be employed.

Alternatively the anhydride may be formed with a phosphorus acid, for example by reaction under substantially anhydrous conditions of the carboxyl group with a phosphorus trihalide such as phosphorus trichloride, preferably in an inert solvent such as a halogenated hydrocarbon or a cyclic ether in the presence of a base such as a tertiary amine, for example as described In Belgian Pat. No. 781,749 and French Pat. No. 2,136,200.

N-Formylated cephalosporin starting materials of general formula II may be prepared by formylation of a corresponding 7-aminocephalosporin acid derivative, for example as described in our British Pat. No. 1,290,327. Thus the 7-aminocephalosporin may be reacted with a conventional formylating agent, such as formic acid and a lower alkanoic anhydride e.g. acetic anhydride, a lower alkyl orthoformate e.g. methyl orthoformate or ethyl orthoformate, or a formyl halide e.g. formyl fluoride or formyl chloride. Alternatively the 7-aminocephalosporin acid derivative may be re-acted with a formic acid ester, e.g. ethyl formate under reflux, advantegeously in the presence of a bifunctional catalyst such as pyrid-2-one, imidazole or formic acid.

N-Formulated penicillin starting materials of general formula II may be prepared by, for example, reacting the corresponding 6-aminopenicillin with formic acid and a lower alkanoyl halide e.g. acetyl chloride, preferably in the presence of a tertiary organic base such as triethylamine or pyridine. Low temperatures, e.g. in the range −25° to −100° C, such as −50° to −70° C are preferably employed in such formylation reactions.

The carbon atoms in the isocyano group of compounds of general formula I has marked reactivity so that compounds of formula I may be reacted with a wide range of electrophilic species to yield a variety of N-acylated and other N-substituted penicillin and cephalosporin type compounds.

Thus, for example, according to another aspect of this invention, a compound of formula I may be converted to an α-hydroxyacylamido cephalosporin of formula

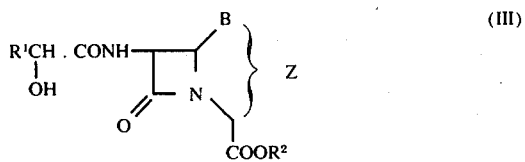

(wherein $R^1$ is a carbocyclic or heterocyclic aryl group, $R^2$ is a hydrogen atom or a carboxyl blocking group, and B and Z have the above-defined meanings) by reaction with an aromatic aldehyde of formula $R^1CHO$ (where $R^1$ has the abovej-defined meaning) in the presence of an acid, this leading to attack by the carbonyl group on the isocyanide carbon atom, followed by treatment of the reaction product with an aqueous medium, e.g. an aqueous solution of a weak inorganic base such as sodium bicarbonate, and, if desired, a deprotection reaction, to yield the desired compound of formula III.

Where the group $R^1$ in the aromatic aldehyde $R^1CHO$ is a carboxylic aryl group this may be, for example, phenyl or substituted phenyl, e.g. phenyl substituted by one or more electron withdrawing groups such as nitro, formyl, carboxy or esterified carboxy. Heterocyclic aryl groups $R^1$ preferably contain at least one 5- or 6-membered ring containing one or more heteroatoms selected from O, N and S, suitable groups including thienyl, furyl, pyridyl, benzofuryl and benzothienyl.

The acid used in the reaction of the compound (I) with the aromtic aldehyde may be, for example, a mineral acid such as hydrochloric or sulphuric acid, 8N-sulphuric acid having proved convenient for this purpose, or a Lewis acid such as boron trifluoride, this conveniently being employed in the form of an etherate.

The conversion of compounds of formula I to a compound of formula III may if desired by conducted in a solvent, preferably an inert organic solvent such as an ether, e.g. tetrahydrofuran or dioxan, or a chlorinated hydrocarbon, e.g. methylene chloride. In many instances, however, the aromatic aldehyde may itself serve as a solvent for the reaction system.

The reaction is desirably carried out at a temperature in the range −30 to +100° C, advantageously +10 to +75° C, conveniently being effected at room temperature. The course of the reaction may be monitored by, for example, thin layer chromatography.

When it is desired to remove a blocking group R after transformation of the isocyanide group, the free carboxyl group maybe regenerated from an ester by any of the usual methods. Thus, for example, acid and base-catalysed hydrolysis is generally applicable, as are enzymically-catalysed hydrolyses; however, aqueous mixtures may be poor solvents for these compounds and they may cause isomerizations, rearrangements, side-reactions, and general destruction, so that special methods may the desirable.

Five suitable methods of deesterification are
1. Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole.

2. Reduction.

Suitable systems for effecting reduction are zinc/acetic acid, zinc/formic acid, zinc/lower alcohol, zinc-/pyridine, palladised-charcoal and hydrogen, and sodium and liquid ammonia.

3. Attack by nucleophiles.

Suitable nucleophiles are those containing a nucleophilic oxygen or sulphur atom, for example alcohols, mercaptans and water.

4. Oxidative methods, for example, those which involve the use of hydrogen peroxide and acetic acid.

5. Irradiation.

Where the carboxyl blocking group R is an anhydride with a carboxylic, phosphorus or other acid, the blocking group may be removed by simple hydrolysis using, for example, water or aqueous acid. The use of anhydride blocking groups is particularly advantageous in view of their subsequent ease of removal.

Where at the end of a given preparative sequence compounds are obtained wherein B is > S→O and a compound is desired in which B is > S conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Alternatively, reduction of the 1-sulphinyl group may be effected by phosphorus trichloride or tribromide in solvents such as methylene chloride, dimethylformamide or tetrahydrofuran, preferably at a temperature of −20° C to +50° C.

Where the compound of general formula I or a product obtained therefrom by reaction of the isocyano group is a ceph-2-em derivative, this may, if desired, be converted to the corresponding ceph-3-em derivative by treatment with a base.

The 3-substituent P of the above cephalosporin compounds of formula Ia and the corresponding starting materials may be a saturated or unsaturated, substituted or unsubstituted organic group containing 1–20 carbon atoms.

Preferred unsubstituted organic groups P include lower alkyl groups such as methyl or ethyl and aryl lower alkyl groups such as benzyl. Unsaturated organic groups include vinyl and substituted vinyl groups, e.g. those having the formula

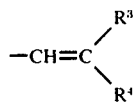

wherein $R^3$ and $R^4$, which may be the same or different, are each hydrogen or a substituted or unsubstituted aliphatic (e.g. alkyl, preferably $C_1$-$C_6$ alkyl such as methyl, ethyl, iso-propyl, n-propyl etc.), $C_5$-$C_7$ cycloaliphatic (e.g. cyclopentyl or cyclohexyl), $C_7$-$C_{10}$ araliphatic (e.g. benzyl or phenylethyl), $C_6$-$C_{12}$ aromatic (e.g. phenyl or nitrophenyl) group, nitrile or lower alkoxycarbonyl.

When P is a substituted methyl group it may be depicted by the formula

wherein Y is an atom or group e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry.

When Y is the residue of a nucleophile it may be inter alia a halogen atom (i.e. chlorine, bromine or iodine), an ether group (e.g. an alkoxy group, preferably a lower alkoxy group such as methoxy) or a thioether group as described in Belgian Pat. Nos. 719,711; 719,710; 734,532 and 734,533.

Preferred thioether groups Y include those having the formula $R^5S$— wherein $R^5$ is aliphatic, e.g. lower alkyl such as methyl, ethyl, n-propyl etc. or lower alkanoyl such as acetyl; araliphatic, e.g. aryl lower alkyl such as benzyl, phenethyl etc. or substituted phenyl lower alkyl; alicyclic e.g. cycloalkyl such as cyclopentyl or cyclohexyl; or carbocyclic or heterocyclic aryl e.g. phenyl, substituted phenyl, or a heterocyclic group containing at least one 5- or 6-membered ring and having one or more heteroatoms selected from O, N and S. Such heterocyclic groups $R^5$ may be substituted, and examples of suitable heterocyclic groups include thiadiazolyl, e.g. 5-methyl-1,3,4-thiadiazol-2-yl; diazolyl; triazolyl; tetrazolyl, e.g. 1-methyltetrazol-5-yl, 1-ethyltetrazol-5-yl or 1-phenyltetrazol-5-yl; thiazolyl; thiatriazolyl; oxazolyl; oxadiazolyl, e.g. 2-phenyl-1,3,4-oxadiazol-5-yl; pyridyl; pyrimidyl; fused heterocyclic ring systems such as benzimidazolyl, benzoxazolyl, benzothiazolyl, triazolopyridyl or purinyl; and substituted versions of such fused ring systems, e.g. nitrobenzothiazol-2-yl such as 5- or 6-nitrobenzothiazol-2-yl.

Other preferred Y groups include pyridin-1-yl and substituted pyridin-1-yl.

When Y is a derivative of a residue of a nucleophile it may be, for example, an acyloxy group, preferably acetoxy, as described in British Pat. No. 1,141,293.

Compounds of the process according to the invention wherein Y is the residue of a nucleophile may be prepared by the reaction of a 3-acetoxymethyl cephalosporin compound with a nucleophile, for example, pyridine or other tertiary amine as described in British Pat. No. 912,541; a sulphur linking, nitrogen-linking or inorganic nucleophile as described in British Pat. No. 1,012,943; a sulphur-linking nucleophile as described in British Pat. Nos. 1,059,562; 1,101,423 and 1,206,305; a nitrogen-linking nucleophile as described in British Pat. Nos. 1,030,630; 1,082,943 and 1,082,962. This list is not limiting and is given purely by way of illustration. Compounds of the invention wherein Y is the residue of a nucleophile may also be prepared by the reaction of a 3-halomethyl-cephalosporin with any of the nucleophiles disclosed in the above references, such a process being described in Belgian Pat. No. 719,711.

Where Y is a halogen (i.e. chlorine, bromine or iodine) ceph-3-em starting compounds may be prepared by halogenation of a 7β-acylamido-3-methylceph-3-em-4-carboxylic acid ester 1β-oxide followed by subsequent reduction of the 1β-oxide group as described in Belgian Pat. No. 755,256.

The corresponding ceph-2-em compounds may be prepared by the method of Dutch published Pat. Application No. 6,902,013 by reaction of a ceph-2-em-3-methyl compound with N-bromo-succinimide to yield the ceph-2-em-3-bromomethyl compound.

Where Y is a hydrogen atom the compound may be prepared by the method described in British Pat. No. 957,569 or from a penicillin compound by the method described in U.S. Pat. Specification No. 3,275,626 and Belgian Pat. Nos. 747,119 and 747,120.

Certain compounds of formulae II and III are novel and constitute a further feature of the invention, these compounds including:

Diphenylmethyl (6R,7R)-3-acetoxymethyl-7-formamido ceph-3-em-4-carboxylate;

Diphenylmethyl (6R,7R)-3-(1-methyltetrazol-5-ylthiomethyl)ceph-3-em-4-carboxylate;

Sodium (3S,5R,6R)-6-formamido-2,2-dimethylpenam-3-carboxylate;

p-Nitrobenzyl(3S,5R,6R)-6-formamido-2,2-dimethylpenam-3-carboxylate;

Diphenylmethyl (2'ζ,6R,7R)-7-(2'-hydroxy-2'-phenylacetamido)-3-methylceph-3-em-4-carboxylate;

Diphenylmethyl (6R,7R,2' R and S)-7-[2'-hydroxy-2'-(p-nitrophenyl)acetamido]-3-methylceph-3-em-4-carboxylate;

(6R,7R,2'S)-7-[2'-Hydroxy-2'-(p-nitrophenyl)acetamido]-3-methylceph-3-em-4-carboxylic acid;

Diphenylmethyl (6R,7R,2'R and S)-7-[2'-hydroxy-2'-(thien-2-yl)acetamido]-3-methylceph-3-em-4-carboxylate;

(6R,7R,2'R and S)-7-[2'-hydroxy-2'-hydroxy-2'-(fur-2-yl)acetamido]-3-methylceph-3-em-4-carboxylic acid and the sodium salt and diphenylmethyl ester thereof;

Diphenylmethyl (6R,7R,2'R and S)-3-acetoxymethyl-7-[2'-hydroxy-2'-(p-nitrophenyl)acetamido]-ceph-3-em-4-carboxylate;

Diphenylmethyl (6R,7R,2'R and S)-7-(2'-hydroxy-2'-phenylacetamido)-3-(5-methyl-1,3,4-thiadiazol-2-ylthiomethyl)ceph-3-em-4-carboxylate;

(6R,7R,2'S)-7-(2'-hydroxy-2'-phenylacetamido)-3-(5-methyl-1,3,4-thiadiazol-2-ylthiomethyl)ceph-3-em-4-carboxylic acid;

(6R,7R,2'R and S)-7-[2-Hydroxy-2'-(fur-2-yl)acetamido]-3-(5-methyl-1,3,4-thiadiazol-2-ylthiomethyl) ceph-3-em-4-carboxylic acid and the diphenylmethyl ester thereof;

Diphenylmethyl (6R,7R,2'S)-7-2'-hydroxy-2'-(thien-2-yl)acetamido]-3-(5-methyl-1,3,4-thiadiazol-2-ylthiomethyl)ceph-3-em-4-carboxylate; and Diphenylmethyl (6R,7R,2'R and S)-7-(2'-hydroxy-2'-phenylacetamido)-3-(1-methyltetrazol-5-ylthiomethyl)ceph-3-em-4-carboxylate.

The following examples illustrate the invention. All temperatures are in ° C. Melting points were measured on a Kofler block and are uncorrected. Optical rotations were measured in chloroform solution between +20 and +27° at concentrations of 1 ± 0.3%. Ultraviolet spectra were measured on ethanol solutions. Infrared spectra were recorded in bromoform solution. N.m.r. spectra were recorded at 60 or 100 MHz in deuteriochloroform. Signs of coupling constants are not assigned ($s$ = singlet, $d$ = doublet, $dd$ = double doublet, $t$ = triplet, $q$ = quartet, $m$ = multiplet). Integrals agreed with assignments. Organic solutions were dried by standing over anhydrous magnesium sulphate. Solids were dried in vacuo at room temperature (ca. 1 mm/25°); analytical samples were dried at +40° in vacuo. Methylene chloride, tetrahydrofuran and N,N-dimethylformamide were dried by passage through a column of basic alumina (Woelm activity 1).

Example 1

Nitrobenzyl (3S,5R,6R and S)-6-Isocyano-2,2-dimethylpenam-3-carboxylate

A solution of p-nitrobenzyl (3S,5R,6R)-6-formamido-2,2-dimethylpenam-3-carboxylate (1.469 g., 3.87 mole) in methylene chloride (40 ml.) was cooled to −60°. To this cold solution was added pyridine (0.622 ml., 7.7 mmole), and then a cold (−60°) solution of phosgene (381 mg., 3.85 mmole) in methylene chloride (3.24 ml.). The mixture was stirred at −60° for 5 min. and then quenched by adding water (10 ml.) at −60°; the temperature was allowed to rise to 0° and the solution washed with water (4 × 50 ml.), dried and evaporated. The residual foam was chromatographed on silica gel (40 g.) in benzene-ethyl acetate (9:1) to give the title compound (as a 7:3 mixture of 6R and 6S isomers respectively, and which contained hydrocarbon contaminants to the extent of ca. $(CH_2)\frac{3}{4}$) as a yellow foam (506 mg., 1.36 mmole, 35.2%); $[\alpha]_D$ + 167.0°; $\lambda_{max}$ 262 nm ($\epsilon$10,440); $\nu_{max}$ 2160 (RN C), 1792 (azetidin-2-one), 1745 ($CO_2R$), 1527 and 1348 cm.$^{-1}$ (Ar-No-hd 2); $\tau$1.70, 2.40 (4H, AB-q, J 8.5 Hz, p-nitrophenyl), 4.42 (0.7H, $d$, J 4.5 Hz.) and 4.82 (0.7H, $d$, J 4.5 Hz.) ($C_5$-H and $C_6$-R-H), 4.50 (0.3H, d, J 2 Hz.) and 5.26 (0.3H, d, J Hz.) ($C_5$-H and $C_6$-S-H), 4.66 (2H, s, $CH_2C_6H_4NO_2$), 5.34 (1H, s, $C_3$-H), 8.30 (2.1H, s) and 8.50 (2.1H, s) ($C[CH_3]_2$, 6R-compound), 8.38 (0.9H, s) and 8.54 (0.9H, s) (c[$CH_3]_2$, 6S-compound), 8.71, 9.10 (1.5H, hydrocarbon impurity). (Found: C, 54.0, 53.6; H, 4.5, 4.5; N, 10.7, 11.0; S, 8.3. $C_{16}H_{15}N_3O_5S.^3/_4$ ($CH_2$) (371.9) requires: C, 53.9; H, 4.5; N, 11.3; S, 8.6%). Also isolated from the column was a sample of the starting material as a white foam (also containing hydrocarbon impurities to the extent of ($CH_2$) 1/$_{20}$) (654 mg., 1.72 mmole, 44.4%) $[\alpha]_D$ + 175.5°, $\lambda_{max}$ 262 nm ($\epsilon$9,760); the i.r. and n.m.r. spectrum resembled those of a standard sample, except that the n.m.r. spectrum indicated the presence of the hydrocarbon impurity.

EXAMPLE 2

Diphenylmethyl (6R, 7R)-7-Isocyano-3-methylceph-3-em-4-carboxylate

A solution of phosgene (3.27 g, 33 mmole) in methylene chloride (ca. 25 ml.) at −20° was added to a stirred solution of diphenylmethyl (6R, 7R)-7-formamido-3-methyl-ceph-3-em-4-carboxylate (prepared as described in Belgian Patent Specification No. 761,897) (12.24 g., 30 mmole) in methylene chloride (500 ml.) containing pyridine (12 ml., 150 mmole), at −20°. The solution was washed with water (2 − 250 ml.) and the organic layers combined with the methylene chloride backwash (250 ml.) of the aqueous layers, dried, and evaporated to a brown foam, which was then dissolved in ethyl acetate (100 to 150 ml.). This solution was added to petroleum-ether (b.p. 40° to 60°) to precipitate the product, which was isolated by filtration and dried to give the title compound as a pale-pink solid (9.539 g., 24.4 mmole, 81.5%); m.p. 117° − 118°; $[\alpha]_D$ ± 0°; $\lambda_{max}$ 252.5 nm ($\epsilon$ 7,030); $\lambda_{inf}$ 257,263.5 nm ($\lambda$ 6,690; 6,480); $\nu_{max}$ 2150 (C=N), 1795 (azetidin-2-one), 1722 ($CO_2R$), 1498, 752 and 735 cm.$^{-1}$ ([$C_6H_5]_2CH$); 2.40 to 2.80 (m, [$C_6H_5]_2CH$), 3.04 (s, [$C_6H_5]_2CH$), 4.88 (d, J 4.5 Hz, $C_7$-H, 5.10 (d, J 4.5 Hz, $C_6$-H), 6.69 (s, $C_2$-$H_2$), 7.81 (s, $C_3$-$CH_3$). (Found; C, 67.2; H, 4.8; N, 6.9; S, 8.1; $C_{22}H_{18}N_2O_3S$ (390.4) requires: C, 67.6; H, 4.6; N, 7.2; S, 8.2%).

EXAMPLE 3 a. Diphenylmethyl (6R,7R)-3-Acetoxymethyl-7-formamido-ceph-3-em-4-carboxylate.

A solution of (6R,7R)-3-acetoxymethyl-7-formamidoceph-3-em-4-carboxylic acid (6.20g, 20mmole) in dry tetrahydrofuran (150ml) was stirred with a solution of diphenyldiazomethane (20mmole; prepared in ether solution, then evaporated) in dry tetrahydrofuran (20ml) at +20 to +25° for 16 hrs. The solvent was evaporated and the solution of the residue in methylene chloride (150ml) was washed successively with 2N-hydrochloric acid 3%-aqueous sodium bicarbonate solution. The solution was dried and evaporated leaving a foam which was chromatographed on kieselgel G (250g) in benzeneethyl acetate (9:1, then 1:1). The appropriate fractions were combined, evaporated, and triturated with ethyl acetate to give the title compound as a crystalline solid (3.789g, 8.1mmole, 40%), m.p. 158.6 to 160.4(cap.); $[\alpha]_D$ +32.8; $\lambda_{max}$261 nm ($\epsilon$7,750); $\nu_{max}$ 3410 (NH), 1788 (azetidin-2-one), 1732 $OCOCH_3$), 1705 ($CO_2R$) and 1698 and 1502 cm$^{-1}$ (CONH); $\tau$ 1.80 (1H,d,J9Hz, NH), 2.70(10H,m, ]$C_6H_5$]CH), 3.03(1H,s, ]$C_6H_5]_2CH$), 4.10 (1H,dd,J9 ; and 4.5Hz, $C_7$-H), 4.90 and 5.23 (2H, ABq, J14Hz, $CH_2OCOCH_3$), 5.04 (1H, d, J5Hz, $C_6$-H), 6.38 and 6.72 (2H, ABq, J18Hz, $C_2$-$H_2$), 8.00 (3H,s, $OCOCH_3$). (Found: C, 62.1; H,4.8; N,5.8; S,6.9. $C_{24}H_{22}N_2O_6$ S(466.5) requires C, 61.8; H,4.8; N,6.0; S,6.9%).

A further preparation of the title compound provided a total yield of 85% in three crops.

b. Diphenylmethyl (6R,7R)-3-Acetoxymethyl-7-isocyanoceph-3-em-4-carboxylate

Pyridine (8.1ml, 100mmole) and a solution of phosgene (2.94g, 29.7mmole) in dry methylene chloride (3.5ml) at −60° were added successively to a cold (−70°) solution of diphenylmethyl (6R,7R)-3-acetoxymethyl-7-formamidoceph-3-4-carboxylate (9.301g, 19.96mmole) in dry methylene chloride (150ml), under a dry nitrogen atmosphere. The reaction was allowed to warm to 0° and then partitioned between ethyl acetate (300ml) and water (100ml). The organic layer was washed with water (100ml) and combined with the ethyl acetate backwash (50ml) of the combined aqueous layers, dried, and then evaporated. The residual foam was dissolved in ethyl acetate (ca 50ml) and the solution slowly added to rapidly stirred petroleum ether (b.p. 60° to 80°). The petroleum ether was decanted from the precipitated solid which was dissolved in ethyl acetate (100ml). The solution was evaporated leaving the title compound as a pale-brown foam containing $1/5$ mole-equivalent of ethyl acetate (n.m.r., microanalysis) (7.176g, 15.4mmole, 77%), $\lambda_{max}$ 250.5nm ($\epsilon$7,160); $\nu_{max}$ 2153 (C N-), 1805 (azetidin-2-one), 1740 (OCOCH$_3$) and 1730 cm$^{-1}$ (CO$_2$R); $\tau$ 2.66 (10H,s, [C$_6$H$_5$]$_2$CH), 3.02 (1H,s, [C$_6$H$_5$]$_2$CH), 4.81 and 5.12 (2H, 2D,J5Hz, C$_6$-H and C$_7$-H), 4.85 and 5.19 (2H, ABq, J14Hz, CH$_2$OCOCH$_3$), 6.49 (2H, broad s, C$_2$-H$_2$), 7.98 (3H,s, C$_3$-CH$_3$). (Found: C, 63.2, 62.8; H,4.5; N,5.8; S,6.8. C$_{24}$H$_{20}$N$_2$O$_5$S. $1/5$ CH$_3$CO$_2$C$_2$H$_5$ (466.1) requires: C, 63.7; H, 4.65; N,6.0; S,6.9%).

EXAMPLE 4

Diphenylmethyl (6R,7R)-7-Isocyano-3-(5-methyl-1,3,4-thiadiazol-2-yl)-thiomethylceph-3-em-4-carboxylate Diphenylmethyl (6R,7R)-formamido-3-(5-methyl-1,3,4-thiadiazol-2-yl)-thiomethylceph-3-em-4-carboxylate dihydrate (1.98g, 3.45mmole) was dried by evaporating its solution in 1,2-dichloroethane. The residual foam was dissolved in dry methylene chloride (30ml) and stirred at −60° under a dry nitrogen atmosphere. To the solution was added pyridine (1.524ml, 18.8mmole) and then a solution of phosgene (0.409g, 4.13mmole) in dry methylene chloride (ca 4ml). The mixture was left to warm to +5° and then partitioned between ethyl acetate (100ml) and water (30ml). The ethyl acetate layer was washed with brine, dried, and evaporated, and the residual solid triturated with ethyl acetate-ether leaving a pale-brown solid. This solid was chromatographed on kieselgel G in methylene chloride - ethyl acetate (3:1) and then triturated with ethyl acetate to give the title compound as a white crystalline solid (906mg, 1.74mmole, 51%); m.p. 174 (dec. only); $\lambda_{max}$ 264nm (saturated solution); $\nu_{max}$2168 (C=N-), 1800 (azetidin-2-one) and 1728 (CO$_2$R), $\tau$2.62(10H,s,[C$_6$H$_5$]$_2$CH), 3.02 (1H,s, [C$_6$H$_5$]$_2$CH, 4.52 (1H, d, J5Hz) and 4.98 (1H,d,JHz)(C$_6$⁻$_H$ and C$_7$⁻$_H$), 5.36 and 5.80 (2H, ABq, J14Hz, CH$_2$SR), 6.21(2H,s,C$_2$-H$_2$), and 7.31 (3H,s, thiodiazolemethyl protons). (Found: C, 57.6; H,4.0; N,10.7; S,18.3. C$_{25}$H$_{20}$N$_4$O$_3$S$_3$ (520.6) requires C, 57.6; H,3.8; N,10.8; S,18.5%).

EXAMPLE 5 a. Diphenylmethyl (6R,7R)-7-Formamido-3-(1-methyltetrazol-5-yl)-thiomethylceph-3-em-4-carboxylate A solution of diphenylmethyl (1S,6R,7R)-3-bromomethyl-7-formamidoceph-3-em-4-carboxylate 1-oxide (503mg, 1mmole) and 1-methyl-5-mercaptotetrazole (114mg, 11mmole) in dry N,N-dimethylformamide (20ml) was stirred at 0° and treated with a solution of triethylamine (0.14ml, 1mmole) in dry N,N-dimethylformamide (5ml) and then allowed to warm to +23°. After stirring at +23° for 1½ hours the solution was cooled to 0° and treated successively with potassium iodide (1.328g, 8mmole) and acetyl chloride (0.28ml, 4mmole) and then stirred at +23° for 16 hours and evaporated. The residue was stirred for 10 mins. with 0.16M-sodium metabisulphite (50ml) and the resulting solid filtered off and triturated with methanol (25ml) to give the title compound as an off-white solid (374mg, 71.5%); $\lambda_{max}$(CHCl$_3$) 264.5nm, inflexion at 274.5nm ($\epsilon$ 8,200 and 7,500); $\nu_{max}$ (Nujol) 3240 and 3200 (NH), 1772(azetidin-2-one), 1717(CO$_2$R) and 1658 and 1528 cm$^{-1}$ (COHN); $\tau$(Me$_2$SO-D$_6$) 0.88(1H,d J9Hz NH), 1.78 (1H,s,CHO), 2.50(10H,m, [C$_6$H$_5$]$_2$CH),3.05(1H,s,[C$_6$H$_5$]$_2$CH), 4.08 (1H,dd, J9 and 4.5Hz, C$_7$-H), 4.78(1H,d,J4.5Hz, C$_6$-H), 5.57 and 5.82(2H, ABq, J 13.5Hz, CH$_2$SR), 6.10 (3H,s, tetrazole methyl protons) and 6.20 (2H,m,C$_2$-H$_2$).

b. Diphenylmethyl (6R,7R)-7-Isocyano-3-(1-methyltetrazol-5-ylthiomethyl)ceph-3-em-4-carboxylate A suspension of diphenylmethyl (6R,7R)-7-formamido-3-(1-methyltetrazol-5-yl)-thiomethylceph-3-em-4-carboxylate (470mg, 0.894mmole) in pyridine (30ml) was stirred and cooled to −30 to −40° whilst a slow stream of phosgene was bubbled through it for 1 min. The mixture was then warmed to 0°, which caused all the solid to dissolve, and then poured into water (2 liters). The precipitated solid was filtered off and then stirred with methylene chloride and refiltered. The filtrate was evaporated and the residue was chromatographed on kieselgel G (15g) in methylene chloride-ethanol (97:3). The title compound was isolated from the appropriate fractions, as a pale-brown foam (283mg, 0.562mmole, 63%), $\epsilon_{max}$ 258.5nm ($\epsilon$8,400); $\nu_{max}$(Nujol) 2170 (C N-), 1800(azetidin-2-one) and 1728 (CO$_2$R); $\tau$ 2.64(10H,m, ]C$_6$H$_5$]$_2$CH), 3.03 (1H,s,]C$_6$H$_5$]$_2$CH), 4.75(1H,d,J4.5Hz) and 5.05 (1H,d,J4.5Hz) (C$_6$-H and C$_7$-H),5.45 and 5.76(2H, ABq, J13Hz, CH$_2$SR), 6.15(3H,s, tetrazole methyl protons), 6.19(2H,s, C$_2$-H$_2$). (Found: C,56.4, 56.8; H,4.1,4.2; N,15.5, 15.8; S,12.1. C$_{24}$H$_{20}$N$_6$O$_3$S$_2$ (504.6) requires: C, 56.6; H,4.0; N,16.7;S,12.7%).

EXAMPLE 6 a. Diphenylmethyl (2'ζ,6R,7R)-7-(2'-Hydroxyphenylacetamido)-3-methylceph-3-em-4-carboxylate Diphenylmethyl (6R,7R)-7-isocyano-3-methylceph-3-em-4-carboxylate (390 mg., 1 mmole), 8N-sulphuric acid (0.125 ml., 1 mmole) and benzaldehyde (1.6 ml.) were stirred together at +20 to 25° for 2 hours. The mixture was then diluted with methylene chloride (25 ml.), washed with dilute sodium bicarbonate solution, dried, and evaporated at 40°/ca. 20 mm, then 50°/0.5 to 1 mm. The residual oil was chromatographed on silica gel (12 g.) in benzene-ethyl acetate (4:1) to give the title compound containing ca. 1.5 mole-equivalent of water (164.7 mg., 0.32 mmole, 32%) as a white foam [$\alpha$]$_D$ + 46.2°; $\lambda_{max}$ 257.5 nm ($\epsilon$ 6,970); $\nu_{max}$ 3610 (OH), 3420 (NH), 1783 (azetidin-2-one), 1723 (CO$_2$R), 1690 and 1518 (CONH), 750 and 730 cm.$^{-1}$ (Ph$_2$CH); $\tau$ 2.40 to 2.80 (m,]C$_6$H$_5$]$_2$CH,C$_6$H$_5$ CHOH and NH), 3.06 (s, ]C$_6$H$_5$]$_2$CH), 4.31 (dd, J 9, 4.5 Hz, C$_7$-H), 4.89 (s, C$_6$H$_5$CHOH), 5.08 (d, J 4.5 Hz, C$_6$-H), 6.40 to 6.90(broad signal, C$_6$H$_5$CHOH), 6.78 (s, C$_2$-H$_2$), 7.92 (s, C$_3$-CH$_3$); signals at 5.89, 7.96 and 8.76 revealed the presence of ca. 0.25 mole of ethyl acetate). Found: C, 63.9, 64.3; H, 4.9, 4.7; N, 5.1; S, 5.5. C$_{29}$H$_{26}$N$_2$O$_5$S. 0.25 CH$_3$CO$_2$C$_2$H$_5$ . 1.5 H$_2$O requires C, 64.0; H, 5.5; N, 5.0; S, 5.7%).

An anhydrous sample of the title compound prepared in similar manner to the hydrated product exhibited [$\alpha$]$_D$ + 46.2°; $\lambda_{max}$ 257 nm ($\epsilon$ 6,590); i.r. spectrum closely resembling that of the hydrated product; n.m.r. spectrum identical to the hydrated product except that $\tau$ 4.89 signal replaced by 4.89 (1H, d, J 3.5 Hz, C$_6$H$_5$CHOH) and $\tau$ 6.40 to 6.90 signal replaced by 6.30 (1H, d, J 3.5 Hz, C$_6$H$_5$CHOH). (Found: C, 67.8, 67.4; H, 5.2; 5.1; N, 5.1, 5.2; S, 5.9. C$_{29}$H$_{26}$N$_2$O$_5$S (514.6) requires C, 67.6; H, 5.1; N, 5.5; S, 6.2%).

b. (6R,7R,2'R and S)-7-(2'-Hydroxyphenylacetamido)-3-methylceph-3-em-4-carboxylic Acid A solution of diphenylmethyl (6R,7R,2'and S)-7-(2'-hydroxyphenylacetamido)-3-methylceph-3-em-4-carboxylate (529mg, 1.03mmole) in trifluoroacetic acid (1.3ml) was stirred at +20 to +25° for 10mins, and then evaporated. The residual oil was dissolved in ethyl acetate (50ml) and washed with 3%-sodium bicarbonate solution (3×15ml). The combined aqueous layers were washed with ethyl acetate (3×15ml), then covered with ethyl acetate (50ml) and adjusted to pH2.5. The ethyl acetate layer was combined with the ethyl acetate wash (15ml) of the aqueous layer, dried, and evaporated, leaving the title compound (as a 5:3=S:R-mixture of diastereomers, [nmr]) as a foam containing ½ mole-equivalent of ethyl acetate (nmr and microanalysis) and 2mole-equivalents of water (i.r. and microanalysis) (258 mg, 0.60mmole, 58%); $\lambda_{max}$ 257.5nm, inflexions at 254 and 262.5nm ($\epsilon$5,870; 5,780 and 5,830 respectively); $\nu_{max}$ 3640 (OH, H$_2$O), 3450 (NH), 1784 (azetidin-2-one), 1730 (CO$_2$H) and 1690; and 1510 cm$^{-1}$ (CONH); $\tau$ assignments of minor component (2'R) follow those of the major component (2'S) 1.52 and 1.36 (total 1H, 2D, J 9Hz, NH), 2.40 to 2.73 (5H,m,C$_6$H$_5$), 4.36 and 4.33 (total 1H,2D, J9 ; and 4.5Hz, C$_7$-H), 4.90 and 4.83 (total 1H,2S,C$_6$H$_5$CH), 4.93 and 4.98 (total 1H, 2d, J4.5Hz, C$_6$-H), 6.51(S) and 6.38 and 6.64 (Abq J18Hz) total 2H,C$_2$-H$_2$), 7.95 (3H,C$_3$-CH$_3$), and signals at 5.91, 7.98 and 9.78 revealed the presence of ½mole-equivalent of ethyl acetate. (Found: C,50.7; H,4.9; N,6.0 and 6.1; S,7.3. C$_{16}$H$_{16}$N$_2$O$_5$S. ½ CH$_3$CO$_2$C$_2$H$_5$. 2H$_2$O (428.4) requires C,50.4; H,5.6; N,6.5;S,7.5%).

EXAMPLE 7 a. Diphenylmethyl (6R,7R,2'R)-7-[2'-Hydroxy-(p-nitrophenyl)-acetamido]-3-methylceph-3-em-4-carboxylate Diphenylmethyl (6R7R)-7-isocyano-3-methylceph-3-em-4-carboxylate (390mg, 1mmole), boron trifluoride diethyl etherate (0.125ml, 1mmole), and p-nitrobenzaldehyde (151mg, 1mmole) were stirred in tetrahydrofuran (3ml) for 2 hours at +20 to +25°. Ethyl acetate (30ml) was then added and the solution was washed with 3%-sodium bicarbonate solution (20ml), then dried and evaporated. Chromatography of the residue on kieselgel G (15g) in benzene-ethyl acetate (2:1) provided the title compound as a foam (32.4mg, 0.058mmole, 5.8%), t.1.cRf (benzene:ethyl acetate = 1:1) 0.40; $\tau$ (CDCl$_3$) 1.80 and 2.38 (4H, ABq, J9Hz, O$_2$N-C$_6$H$_4$), 2.60 to 2.80 (10H, broad s, CH[C$_6$H$_5$]$_2$), 3.07 (1 H,s,CH]C$_6$H$_5$]$_2$), 4.33 (1H, dd, J9 and 4.5Hz, C$_7$-H), 4.76 (1H,s, O$_2$N-C$_6$H$_4$CH), 5.05 (1H,d,J4.5Hz, C$_6$-H), 6.58 and 6.91 (2H, ABq, J18Hz, C$_2$-H$_2$), 7.91 (3H,s, C$_3$-CH$_3$).

b. Diphenylmethyl (6R,7R,2'S)-7-[2'-Hydroxy-(p-nitrophenyl)-acetamido]-3-methylceph-3-em-4-carboxylate The title compound (81 mg, 0.145mmole, 14.5%) was obtained from the chromatography described in (a) above, tlc Rf (benzene:ethyl acetate = 1:1)0.47; $\tau$ 1.80 and 2.35 (4H, ABq, J9Hz, O$_2$N-C$_6$H$_4$), 2.60 to 2.80 (10H, broad s, CH[C$_6$H$_5$]$_2$), 3.06 (1H,s,CH[C$_6$H$_5$]$_2$), 4.32 (1H,dd,J9 and 4.5Hz, C$_7$-H), 4.76(1H,s,CHOH),5.11 (1H,d,J 4.5Hz, C$_6$-H), 5.08 (1H,broad s, CHOH), 6.80 (2H, broad s, C$_2$-H$_2$), 7.91 (3H,s, C$_3$-CH$_3$).

c. (6R,7R,2'S)-7-[2'-Hydroxy-(p-nitrophenyl)-acetamido]-3-methylceph-3-em-4-carboxylic Acid Diphenylmethyl (6R,7R,2'S)-7-[2'-hydroxy-(p-nitrophenyl)-acetamido]-3-methylceph-3-em-4-carboxylate (397.5 mg, 0.71 mmole) was treated with trifluoroacetic acid (2ml) for 7 mins. at +20 to +25°. The trifluoroacetic acid was evaporated and the residue was dissolved in ethyl acetate (25ml) and extracted with 3% sodium bicarbonate solution (2×20ml). The combined aqueous layers were washed with ethyl acetate (3×20ml), covered with ethyl acetate (50ml) and adjusted to pH 2.5. The ethyl acetate layer was combined with the ethyl acetate washes (3×20ml) of the aqueous layer, dried, and evaporated. The title compound was isolated in a similar manner, as a foam containing ⅔ mole equivalent ethyl acetate (nmr, microanalysis) and 1 mole equivalent water (ir, microanalysis), (204mg, 0.434mmole, 61%); $\lambda_{max}$266.5nm ($\epsilon$ 15,210); $\lambda_{max}$ (Nujol) 3600(OH,H$_2$O), 3330(NH),2600(CO$_2$H), 1760 (azetidin-2-one), 1710 (CO$_2$H), and 1676 and 1520cm$^{-1}$ (CONH); $\tau$(Me$_2$SO-D$_6$) 1.28 (1H,d,J8.5Hz, NH), 1.73 and 2.22 (4H, ABq, O$_2$NC$_6$H$_4$), 4.40 (1H, dd, J8.5 and 4.5Hz, C$_7$-H), 4.69 (1H,s,O$_2$N C$_6$H$_4$CH), 4.95 (1H,d,J4.5Hz, C$_6$-H), 6.39 and 6.67 (2H, ABq, J 18Hz, C$_2$-H$_2$), 7.95 (3H,s,C$_3$-CH$_3$)$_,$ and signals at 5.95, 8.00 and 8.80 revealed the presence of ⅔ mole-equivalents of ethyl acetate. (Found: C,48.2, 48.3; H,4.2; N,8.9; S,6.5. C$_{16}$H$_{15}$N$_3$O.S. ⅔ CH$_3$CO$_2$C$_2$H$_5$. H$_2$O (470.1) requires C,47.6; H,4.8; N,8.9; S,6.8%).

EXAMPLE 8 a. Diphenylmethyl (6R,7R,2′R and S)-7-[2′-Hydroxy-2′(thien-2-yl)-acetamido]-3-methyl-ceph-3-em-4-carboxylate A solution of diphenylmethyl (6R,7R)-7-isocyano-3-methylceph-3-em-4-carboxylate (622mg, 1.59mmole) in dry tetrahydrofuran (5ml) was added to a solution of thiophene-2-carboxaldehyde (184mg, 1.61mmole) and boron trifluoride diethyl etherate (0.199ml, 1.6mmole) in dry tetrahydrofuran (5ml). After stirring for 18 hours at +20 to +25° ethyl acetate (50ml) was added and the solution washed with 3%-aqueous sodium bicarbonate solution (50ml), dried, and evaporated. The residual oil was purified by chromatography on kieselgel G (25g) in benzene-ethyl acetate (2:1) to give the title compound as a foam (105mg, 2.02mmole, 12.7%); $\tau$ 2.30 to 3.05 (13H,m, CH [$C_6H_5$]$_2$ and thiopheneprotons), 3.07 (1H,s,CH[$_6H_5$]$_2$), 4.30 (1H,dd,J9 and 4.5Hz, $C_7$-H), 4.58 (1H,s,-CHOH), 5.05 (1H,d,J4.5Hz, $C_6$-H), 6.14 (1H,broad s, CHOH), 6.65 and 6.90 (2H, ABq, J18Hz, $C_2$-$H_2$) and 7.93 (3H,s. $C_3$-$CH_3$).

b. Sodium (6R,7R,2′R and S)-7-[2′-Hydroxy-2′-(thien-2-yl)-acetamido]-3-methylceph-3-em-4-carboxylate Diphenylmethyl (6R,7R,2′R and S)-7-(2′- hydroxy-2′-[thien-2-yl]-acetamido)-3-methylceph-3-em-4-carboxylate (543mg, 1.05mmole) was dissolved in anisole (4ml) and stirred with trifluoroacetic acid (4 ml) at +20 to +25° for 7 mins. The anisole and trifluoroacetic acid were evaporated and the residue partitioned between 3%-aqueous sodium bicarbonate solution (ca 50ml) and ethyl acetate (ca 50ml). The aqueous layer was washed with ethyl acetate (3xca 50ml), layered with ethyl acetate and adjusted to pH 2.5. The ethyl layer was combined with the ethyl acetate backwash of the aqueous layer, dried, and evaporated to give (6R,7R,2′R and S)-7-(2′- hydroxy-2′-[thien-2-yl]-acetamido)-3-methylceph-3-em-4-carboxylic acid as a foam (337mg, 91%). This foam was dissolved in acetone (3ml) and stirred with a solution of sodium 2-ethylhexanoate (186mg, 1.05 mmole) in acetone (2ml) and ether (2ml). The precipitated material was filtered off, washed with ether, and dried to give the title compound containing 2mole-equivalents of water (i.e., microanalysis)and 1/6 mole-equivalents of ether (n.m.r., microanalysis) as a pale-brown solid (183mg, 0.486 mmole, 46.4%); $\lambda_{max}$ (pH6-buffer) 237.5nm, inflexion at 255nm ($\epsilon$12,640 and 9,250 respectively); $\nu_{max}$ (nujol) 3380 (NH,$H_2O$), 1760 (azetidin-2-one), 1680 and 1528 (CONH), and 1600 cm$^{-1}$ ($CO_2$-); $\tau$ (Me$_2$SO-D$_6$) 1.48 and 1.63 (total 1H, 2D,J9Hz,NH), 2.54 to 3.10 (3H, m, thiophene protons), 4.46 (ca 1H, m, $C_7$-H), 4.60 and 4.62 (total ca 1H, 2S, CHOH), 5.00 (1H,d,J4.5Hz, $C_7$-H), 6.49 and 6.87 (2H, ABq, J18Hz, $C_2$-$H_2$), 8.01 (3H,s, $C_3$-$CH_3$). A signal at $\tau$8.89 revealed the presence of 1/6 mole-equivalent of diethyl ether. (Found: C,41.1, 41.4; H,3.6, 3.8;N,6.6, 7.0;S,14.5. $C_{14}H_{13}N_2NaO_5S_2$. 1/6 $C_2H_5OC_2H_5$. $2H_2O$ (424.7) requires C,41.5; H,4.4; N,6.5; S,15.1%).

EXAMPLE 9 a. Diphenylmethyl (6R,7R,2′R and S)-7-[2′-Hydroxy-2′-(fur-2-yl)-acetamido]-3-methyl-ceph-3-em-4-carboxylate A solution of diphenylmethyl (6R,7R)-7-isocyano-3-methylceph-3-em-4-carboxylate (11.70g, 30 mmole) in dry tetrahydrofuran (40ml) was added to a solution of furfuraldehyde (2.88g, 30 mmole) and boron trifluoride diethyl etherate (3.75ml, 30 mmole) in dry tetrahydrofuran (60ml). The mixture was stirred at +20 to +$\cong$° for 24 hours and then worked up and purified as described in Example 8 (a). The title compound was obtained as a foam containing 1/4 mole-equivalent of ethyl acetate (n.m.r., microanalysis) (1.653g, 3.14 mmole, 10.5%); $\lambda_{max}$ 257nm (saturated solution); $\nu_{max}$ 3600 (OH), 3406(NH), 1782 (azetidin-2-one), 1724 ($CO_2R$), and 1696 and 1520 cm$^{-1}$ (CONH); $\tau$2.20 to 2.95 (11H,m, [$C_6H_5$]$_2$CH and fur-5-yl proton), 3.05 (1H,s, [$C_6H_5$]$_2$CH), 3.60 (2H,m,fur-3 and 4-yl protons), 4.24 (1H,m, $C_7$-H), 4.80 (1H,s,-CHOH), 5.04 and 5.08 (total 1H,2d, J4.5Hz, $C_6$-H), 6.63 and 6.89 (2H, ABq, J18Hz, $C_2$-$H_2$), 7.93 (3H,s, $C_3$-$CH_3$). Signals at 5.90, 7.98 and 8.78 revealed the presence of 1/4 mole-equivalent of ethyl acetate. (Found: C,63.4, 63.9; H,4.7, 4.9; N,4.8, 4.9; S,6.1..$C_{27}H_{24}N_2O_6S$. 1/4$CH_3CO_2C_2H_5$ (526.55) requires: C, 63.5; H,5.0; N,5.3; S,6.1%).

b. Sodium (6R,7R,2′R and S)-7-[2′-Hydroxy-2′-(fur-2-yl)-acetamido]-3-methyl-ceph-3-em-4-carboxylate Diphenylmethyl (6R,7R,2′R and S)-7-(2′-[fur-2-yl]-acetamido)-3-methylceph-3-em-4-carboxylate (463mg, 1.365 mmole) was treated with anisole and trifluoroacetic acid in the manner described previously [see Example 10 (b)] to give (6R,7R,2′R and S)-7-[2′-hydroxy-2′-(fur-2-yl)acetamido]-3-methylceph-3-em-4-carboxylic acid as a foam (368mg, 1.09 mmole, 57.3%). The title compound was obtained from the acid (368mg, 1.1 mole) by treatment with sodium 2-ethylhexanoate in acetone and ether, as a pale-brown solid containing 2½mole-equivalents of water (i.r. and microanalysis), (221mg, 0.545 mmole, 50%);$\lambda_{max}$ (pH6 buffer) 220 and 258nm ($\epsilon$10,780 and 8,000 respectively); $\nu_{max}$ (Nujol) 3370 (OH,NH, and $H_2O$), 1755 (azetidin-2-one), 1675 and 1518 (CONH), and 1590 cm$^{-1}$ ($CO_2$); $\tau$(Me$_2$SO-D$_6$) 1.57 and 1.63 (total 1H,2d,J9Hz, NH), 2.37 (1H,s) and 3.59 (2H,m) (furyl protons), 4.44 (1H,m, $C_7$-H), 4.81 and 4.83 (total 1H, 2s, -CHOH), 4.97 (1H,d,J5Hz, $C_6$-H), 6.47 and 6.86 (2H,ABq, J18Hz, $C_2$-$H_2$), 8.00 (3H,s, $C_3$-$CH_3$). (Found: C, 41.2, 41.5; H,3.4, 3.6; N,6.4, 6.5; S,7.8; Na,5.9. $C_{14}H_{13}N_2NaO_6S$.2.5 $H_2O$ (405.3) requires: C, 41.6; H,4.5; N,6.9; S,7.9; Na,5.7%).

EXAMPLE 10 a. Diphenylmethyl (6R,7R,2′R)-3-Acetoxymethyl-7-[2′-hydroxy-(p-nitrophenyl)-acetamido]-ceph-3-em-4-carboxylate A solution of diphenylmethyl (6R,7R)-3-acetoxymethyl-7-isocyanoceph-3-em-4-carboxylate (4.504 g, 10.02 mmole), p-nitrobenzaldehyde (1.517 g, 10.02 mmole), and boron trifluoride diethyl etherate (1.25 ml, 10.02 mmole) in dry tetrahydrofuran (25 ml) was stirred for 3½ hr at +20 to +25°. The mixture was then partitioned between ethyl acetate (100 ml) and 3%- aqueous sodium bicarbonate solution (50 ml). The organic layer was stirred for 2 hr. with anhydrous magnesium sulphate and charcoal (ca 3g each), then filtered through kieselguhr and evaporated. The residual brown foam was chromatographed on kieselgel G (250 g) in benzene-ethyl acetate (2:1) to give the title compound as an orange foam (986.7 mg, 1.6 mmole, 16%);t.l.c.Rf (benzene:ethyl acetate = 2:1) 0.1; $[\alpha]_D$ +47°; $\lambda_{max}$ 262nm ($\epsilon$13,600); $\nu_{max}$ 3460 (OH), 3436 (NH), 1786 (azetidin-2-one), 1730($CO_2R$ and $OCOCH_3$), and 1696 and 1520 $cm^{-1}$ (CONH); $\tau$ 1.80 and 2.36 (4H, ABq, J 9Hz,$O_2NC_6H_4$), 2.65 (10H,s, $[C_6H_5]CH$), 3.05 (1H,s, $[C_6H_5]_2CH$), 4.25 (1H,dd,$J_9$ and 5Hz, $C_7$-H), 4.76 (1H,s,-CHOH), 4.98 and 5.25 (2H,ABq, J14Hz, $CH_2OCOCH_3$), 5.04 (1H,d,J5Hz, $C_6H$), 6.38 and 6.70 (2H,ABq, J18Hz, $C_2$-$H_2$) and 8.02 (3H,s,$OCOCH_3$). Peaks at $\tau$5.90, 7.99 and 8.75 revealed the presence of a trace of ethyl acetate. (Found: C, 61.0; H,4.8; N,6.0, 6.2; S,5.1 $C_{31}H_{27}N_3O_9S$ (617.6) requires: C,60.3; H,4.4; N,6.8; S,5.2%).

b. Diphenylmethyl (6R,7R,2′S)-3-Acetoxymethyl-7-[2′-hydroxy-(p-nitrophenyl)-acetamido]-ceph-3-em-4-carboxylate The title compound was obtained from the chromatography described in (a) above as a white crystalline solid containing 1 mole-equivalent of ethyl acetate (372.5 mg, 0.53 mmole, 5.3%); t.l.c.Rf (benzene:ethyl acetate=2:1) 0.17; $[\alpha]_D$+84°;$\lambda_{max}$ 265 nm ($\epsilon$ 17,400); $\nu_{max}$ 3420 (NH), 3275(OH), 1788 (azetidin-2-one), 1742 ($OCOCH_3$), 1726 ($CO_2R$) and 1666 and 1514 $cm^{-1}$ (CONH); $\tau$1.80 and 2.35 (4H, ABq, J9Hz, $O_2NC_6H_4$), 2.65 (10H,s,$[C_6H_5]_2CH$), 3.05 (1H,s, $[C_6H_5]CH$), 4.21 (1H,dd,J9 and 5Hz, $C_7$H), 4.78 (1H, d, J5Hz, -CHOH, on addition of $D_2O$ this signal became a singlet), 5.00 and 5.22 (2H, ABq, J14Hz, $CH_2$-$OCOCH_3$), 5.05 (1H, d,J5Hz, $C_6$-H), 5.7 (1H,d,J5Hz, -CHOH, this signal disappeared on addition of $D_2O$), 6.48 and 6.73 (2H, ABq, J18Hz, $C_2$-$H_2$), and 8.02 (3H,s, $OCOCH_3$). Signals at 5.90, 7.99 and 8.75 revealed the presence of 1 mole-equivalent of ethyl acetate. (Found: C,59.3, 59.4;H,4.9; N,5.7,5.8; 5,4.5 $C_{31}H_{27}N_3O_9S. CH_3CO_2C_2H_5$ (705.7) requires: C,59.5; H,5.0; N,6.0; S,4.5%).

EXAMPLE 11 a. Diphenylmethyl (6R,7R,2′R)-7-(2′-Hydroxyphenylacetamido)-3-(5-methyl-1,3,4-thiadiazol-2-ylthiomethyl) ceph-3-em-4-carboxylate A mixture of diphenylmethyl (6R,7R)-7-isocyano-3-(5-methyl-1,3,4-thiadiazol-2-ylthiomethyl)ceph-3-em-4-carboxylate (2.605g, 5 mmole), benzaldehyde (121ml), and 8N-sulphuric acid (0.3125 ml, 2.5 mmole) were stirred at +20 to +25° for 15 mins. (tlc in benzene: ethyl acetate=1:1 indicated that reaction was complete after 2 mins). Methylene chloride (ca 50 ml) was added and the resulting solution washed with 3%-aqueous sodium bicarbonate solution (ca 25 ml), dried, and evaporated. A solution of the residual oil in methylene chloride (25 ml) was slowly added to rapidly stirred petroleum ether (b.p. 40° to 60°) and the precipitated solid was collected and dried (3.087g). Chromatography of the solid on kieselgel G (100g) in benzene-ethyl acetate (1:1) and combination of the appropriate fractions with 1,2-dichloroethane as wash solvent, gave the title compound as a foam containing ½mole-equivalent of 1,2-dichloroethane (nmr, microanalysis) (867 mg, 1.25 mmole, 25%); t.l.c. Rf (benzene:ethyl acetate = 1:1) 0.25; $[\alpha]_D$ −149°; $\lambda_{max}$ 268nm ($\epsilon$ 13,000); $\lambda_{max}$ 3610 (NH),3410(NH), 1790 (azetidin-2-one), 1722 ($CO_2R$) and 1695 and 1518 $cm^{-1}$ (CONH); $\tau$ 2.67 (15H,s, $[C_6H_5]_2CH$ and $C_6H_5CHOH$), 3.04 (1H,s, $[C_6H_5]CH$), 4.25 (1H,dd, J9 and 5Hz, $C_7$-H), 4.88(1H,s, $C_6H_5CHOH$), 5.08 (1H,d,J5Hz, $C_6$-H), 5.50 and 5.87 (2H, ABq, J 13Hz, $CH_2SR$), 6.00 (1H, broad s, $C_6H_5CHOH$), 6.39 (2H,s, $C_2$-$H_2$) and 7.39 (3H,s, thiodiazole methyl protons). A singlet at 6.30 revealed the presence of ½ mole-equivalent of 1,2-dichloroethane. (Found: C, 57.3; H,4.4; N,8.0,8.1;S,13.9. $C_{32}H_{28}N_4O_5S_3$. ½$C_2H_4Cl_2$(694.3) requires C, 57.1; H,4.3; N,8.1; S,13.9%).

b. (6R,7R,2′R)-7-(2′-Hydroxyphenylacetamido)-3-(5-methyl-1,3,4-thiadiazol-2-ylthiomethyl)ceph-3-em-4-carboxylic Acid Diphenylmethyl (6R,7R,2′R)-7-(2′-hydroxyphenylacetamido)-3-(5-methyl-1,3,4-thiadiazol-2-ylthiomethyl)ceph-3-em-4-carboxylate containing ½mole-equivalent of 1,2-dichloroethane (511mg, 0.737 mmole) was stirred in anisole (5ml) and trifluoroacetic acid (3ml) at +20 to +25° for 7 mins. The mixture was evaporated and the residue partitioned between ethyl acetate (ca 20ml) and 3%-aqueous sodium bicarbonate solution (ca 20ml). The aqueous layer was washed with ethyl acetate (3 × 20ml), layered with ethyl acetate (20ml), and adjusted to pH 2.5. The organic layer was combined with the ethyl acetate washes (3 × 10 ml) of the aqueous layer, dried, and evaporated to a foam. Trituration of the foam with ether-acetone gave the title compound as a pale-yellow solid containing 1/6 mole-equivalent of ether, ⅛ mole-equivalent acetone (n.m.r and microanalysis) and 3 mole-equivalents of water (i.r. and microanalysis) (226mg, 0.41 mmole, 56%); $[\alpha]_D$−75°($Me_2SO$); $\lambda_{max}$ (pH6-buffer) 269nm ($\epsilon$12,010); $\nu_{max}$ (nujol) 3500 (OH, $H_2O$), 3350 (NH), 2600 ($CO_2H$), 1768 (azetidin-2-one), 1700($CO_2H$), and 1660 and 1500 $cm^{-1}$(CONH); Y($Me_2SO$ -$D_6$)1.26 (1H,d,J9Hz, NH), 2.60(5H,m,$C_6H_5$), 4.26 (1H,dd,J9 and 4.5Hz, $C_7$-H), 4.87 (1H,s, $C_6H_5CH$), 4.90 (1H,d, J4.5Hz, $C_6$-H), 5.42 and 5.75 (2H, ABq, J 13Hz, $CH_2$ SR), 6.20 and 6.41 (2H ABq, J 18Hz, $C_2$-$H_2$), and 7.31 (3H,s, thiadiazole methyl protons). Signals at 6.55 and 8.87 and 7.79 respectively revealed the presence of 1/6 mole-equivalent of ether and ⅛ mole-equivalent of acetone. (Found: C,44.4, 44.6; H,3.8; N,9.7, 10.1; S,16.5. $C_{19}H_{18}N_4O_5S_3$. 1/6 ($C_2H_5$)$_2$ 0.1/8 ($CH_3$)$_2$Co.3-$H_2O$ (551.9) requires: C,43.5; H,4.84; N,10.2; S,17.5%). This product very closely resembled (paper chromatography, n.m.r., i.r., u.v., bioactivity) material prepared by an unambiguous route.

c. Diphenylmethyl (6R,7R,2′S)-7-(2′-Hydroxyphenylacetamido)-3-(5-methyl-1,3,4-thiadiazol-2-ylthiomethyl)ceph-3-em-4-carboxylate The title compound was obtained from the chromatography in (a) above as a foam containing ½mole-equivalent of 1,2-dichloroethane (738mg, 1.064 mmole, 21.3%), tlc Rf (benzene:ethyl acetate = 1:1)0.32; $[\alpha]_D$ −62°; $\lambda_{max}$ 268nm ($\epsilon$ 13,000); $\nu_{max}$ 3610(OH), 3410(NH), 1788 (azetidin-2-one), 1720 ($CO_2R$) and 1690 and 1515 $cm^{-1}$ (CONH); $\tau$ 2.65 (15H,s, $[C_6H_5]_2CH$ and $C_6H_5CHOH$), 3.02

(1H,s,[C₆H₅]₂ CH), 4.24 (1H,dd,J9 and 5Hz C₇-H), 4.86 (1H, broad s, C₆H₅CHOH), 5.08 (1H,d,J5Hz, C₆-H), 5.50 and 5.87 (2H, ABq, J13Hz, CH₂SR), 6.10 (1H, broad s, C₆H₅CHOH), 6.37 (2H;s,C₂-H₂), 7.35 (3H,s, thiadiazole methyl protons). A singlet at 6.30 revealed the presence of ½mole-equivalent of 1,2-dichloroethane (found: C,56.5; 56.9; H,4.4; N,7.8, 8.0; S,13.6%).

d. (6R,7R,2'S)-7-(2'-Hydroxyphenylacetamido)-3-(5-methyl-1,3,4-thiadiazol-2-yl)-thiomethylceph-3-em-4-carboxylic Acid By treating the corresponding diphenylmethyl ester containing ½mole-equivalent of 1,2-dichloroethane (512mg, 0.738 mmole) with trifluoroacetic acid and anisole as described in (b) above, a sample of the title compound was obtained as a pale-yellow solid containing 1/6 mole-equivalent each of acetone and ether (nmr, microanalysis) and 2½mole-equivalents of water (ir, microanalysis) (210mg, 0.385 mmole, 52%); $[\alpha]_D$ − 35° (Me₂SO); $\lambda_{max}$ (pH6-buffer) 270 nm ($\epsilon$12,010); $\nu_{max}$(nujol) 3500 (OH,H₂O), 3350 (NH), 2550(CO₂H), 1770 (azetidin-2-one), 1700 (CO₂H), and 1666 and 1502 cm⁻¹ (CONH); $\tau$(Me₂SO-D₆) 1.39 (1H,d,J9Hz, NH), 2.60(5H,m,C₆H₅), 4.30 (1H,dd, J9, and 4.5Hz, C₇-H), 4.83 (1H,d,J4.5H, C₆-H), 4.93 (1H,s, C₆H₅CH), 5.41 and 5.77(2H, ABq, J14Hz, CH₂SR), 6.18 and 6.40 (2H, ABq, J18Hz, C₂-H₂), 7.30 (1H,s, thiodiazole methyl protons). Signals at 6.50 and 8.84 and 7.88 respectively revealed the presence of 1/6 mole-equivalent each of ether and acetone. (Found: C,44.9, 45.2; H,3.8, 3.9; N,9.9, 10.2; S,17.0. C₁₉H₁₈N₄O₅S₃ · 1/6 (C₂H₅)₂O · 1/6 (CH₃)₂ CO.2½ H₂O (545.5) requires: C,44.3; H,4,7; N,10.3; S,17.6%).

EXAMPLE 12 a. Diphenylmethyl (6R,7R,2'R)-7-[2'-Hydroxy-2'-(fur-2-yl)-acetamido]-3-(5-methyl-1,3,4-thiadiazol-2-ylthiomethyl)ceph-3-em-4-carboxylate A mixture of diphenylmethyl (6R,7R)-7-isocyano-3-(5-methyl-1,3,4-thiadiazol-2-ylthiomethyl)ceph-3-em-4-carboxylate (2.084g, 4 mmole), furfuraldehyde (8ml), and 8N-sulphuric acid (0.25ml, 2 mmole) was stirred for 10 mins. at +20 to +25°, then diluted with ethyl acetate (100ml). The solution was washed with 3%-aqueous sodium bicarbonate solution (2 × 50ml), dried and evaporated. The residue was chromatographed on kieselgel G (100g) in benzene-ethyl acetate (1:1) to give the title compound as a foam (222mg, 0.35 mmole, 8.75%); t.l.c. Rf (benzene:ethyl acetate = 1:1) 0.24; $[\alpha]_D$ −109.5°; $\lambda_{max}$ 266nm ($\epsilon$12,300); $\nu_{max}$ 3496 (NH), 3600 (OH), 1796(azetidin-2-one), 1730 (CO₂R) and 1700, and 1520cm⁻¹ (CONH); $\tau$2.64 (11H,m, [C₆H₅]₂CH and fur-5-yl proton), 3.01 (1H,s, [C₆H₅]₂CH), 3.60 (2H,m, fur-3-and-4-yl protons), 4.13 (1H,dd,J9 and 4.5Hz, C₇H), 4.75 (1H,s, -CHOH), 5.02 (1H,d, J4.5Hz, C₆-H), 5.51 and 5.81 (2H, ABq, J 14Hz, CH₂SR), 6.32 (2H,s, C₂-H₂), 7.33 (3H,s, thiadiazole methyl protons) (Found: C,56.4; H,4.3; N,8.7, S,14.7. C₃₀H₂₆N₄O₆S₃(634.8) requires: C,56.7; H,4.1; N,8.8; S,15.1%).

b. (6R,7R,2'R)-7-[2'-Hydroxy-2'-(fur-2-yl)-acetamido]-3-(5-methyl-1,3,4-thiadiazol-2-ylthiomethyl)ceph-3-em-4-carboxylic Acid.

Diphenylmethyl (6R,7R,2'R)-7-[2'-hydroxy-2'-(fur-2-yl)-acetamido]-3-(5-methyl-1,3,4-thiadiazol-2-ylthiomethyl)-ceph-3-em-4-carboxylate (311mg. 0.49 mmole) was treated with anisole (5ml) and trifluoroacetic acid (3ml) for 7 mins. The mixture was evaporated and the residue partitioned between ethyl acetate (ca 10ml) and 3%-aqueous sodium bicarbonate solution (ca 10 ml). The aqueous layer was washed with ethyl acetate (3 × 10ml), layered with ethyl acetate (20ml), and adjusted to pH 2.5. The organic layer was combined with the ethyl acetate washes (3 × 10 ml) of the aqueous layer, dried, and evaporated, leaving the title compound as a foam (163mg. 0.349 mmole, 71%); $\lambda_{max}$(pH6-buffer) 270nm, ($\epsilon$9,850); $\tau$ (Me₂SO-D₆) 1.33 (1H,d,J9Hz, NH), 2.36 (1H,s,fur-5-yl proton), 3.50 (2H,m,fur-3-and-4-yl protons), 4.22 (1H,dd,J9 and 4.5Hz, C₇-H), 4.85 (1H, d,J4.5 H₂,C₆-H), 4.84(1H,s,-CHOH),5.40 and 5.70 (2H, ABq, J13Hz, CH₂SR), 6.18 and 6.41 (2H, ABq, J18Hz, C₂-H₂), 7.30 (3H,s, thiadiazole methyl protons).

c. Diphenylmethyl (6R,7R,2'S)-7-[2'-Hydroxy-2'-(fur-2-yl)-acetamido]-3-(5-methyl-1,3,4-thiadiazol-2-ylthiomethyl)ceph-3-em-4-carboxylate The title compound was isolated from the chromatography in (a) above as a foam (164mg, 0.258 mmole, 6.5%); t.l.c. Rf (benzene:ethyl acetate = 1:1) 0.31; $[\alpha]_D$ −72°; $\lambda_{max}$ 266nm ($\epsilon$ 12,400); $\nu_{max}$ 3650(NH), 3452(NH), 1788 (azetidin-2-one), 1720 (CO₂R), and 1696 and 1516 cm⁻¹ (COHN); $\tau$2.60 (11H,m, [C₆H₅]₂CH and fur-5-yl proton), 3.01 (1H, s[C₆H₅]CH), 3.60 (2H,m, fur-3-and 4-yl protons), 4.17 (1H,dd,J9 and 4.5Hz, C₇-H), 4.74 (1H, s, CHOH), 4.97 (1H,d, J4.5Hz, C₆-H), 5.45 and 5.80 (2H, ABq, J14Hz, CH₂SR), 6.31 (2H,s, C₂-H₂), 7.34(3H,s, thiadiazole methyl protons). (Found: C,56.4 56.5; H,4.2, 4.3; N,8.1, 8.6; S,14.4).

d. (6R,7R,2'S)-7-[2'-Hydroxy-2'-(fur-2yl)-acetamido]-3-(5-methyl-1,3,4-thiadiazol-2-yl)-thiomethylceph-3-em-4-carboxylic Acid Treatment of the corresponding diphenylmethyl ester (213 mg, 0.335 mmole) with anisole (4ml) and trifluoroacetic acid (2ml) as described in (b) above gave the title compound as a foam (98mg, 0.213 mmole, 63.5%); $\tau$(Me₂SO-D₆) 1.40 (1H,d,J9Hz,NH), 2.40 (1H,s, fur-5-yl proton), 3.60 (2H,m, fur-3-and 4-yl protons), 4.25 (1H,dd, J9 and 4.5Hz, C₇-H), 4.82 (1H,d,J4.5Hz, C₆-H), 4.85 (1H,s, -CHOH), 5.40 and 5.74(2H, ABq, J13Hz, CH₂SR), 6.15 and 6.37(2H, ABq, J18Hz, C₂-H₂), 7.30(3H,s, thiadiazole methyl protons).

EXAMPLE 13 a. Diphenylmethyl (6R,7R,2'S)-7-[2'-Hydroxy-2'-(thien-2-yl)-acetamido]-3-(5-methyl-1,3,4-thiadiazol-2-ylthiomethyl)ceph-3-em-4-carboxylate Diphenylmethyl (6R,7R)-7-isocyano-3-(5-methyl-1,3,4-thiadiazol-2-ylthiomethyl) ceph-3-em-4-carboxylate (3.25g, 6.25 mmole), thiophen-2-carboxaldehyde (12.5ml), and 8N-sulphuric acid (0.39ml, 3.13 mmole) were stirred together for 5 mins. Ethyl acetate was added and the solution was washed with 3%-aqueous sodium bicarbonate solution. The organic layer was dried and evaporated to an oil which was chromatographed on kieselgel G (150g) in benzene:ethyl acetate = 1:1 to give diphenylmethyl (6R,7R,2′R and S)-7-[2′-hydroxy-2′-(thien-2-yl)acetamido]3-(5-methyl-1,3,4-thiadiazol-2-yl)-thiomethylceph-3-em-4-carboxylate as a foam (850mg, 1.31 mmole, 21.8%.), t.l.c. Rf (benzene:ethyl acetate = 1:1) 0.365 and 0.44 (2′S- and 2′R- isomers respectively). Further chromatography provide the title compound as a more polar component (70mg, 0.018 mmole, 1.73%%); τ 2.40 to 3.16 (ca 3H,m, [$C_6H_5$]$_2$CH and thienyl protons), 3.02 (ca 1H,s, [$C_6H_5$]$_2$CH), 4.22 (1H,dd,$J_9$ and 4.5Hz, $C_7$-H), 4.56 (1H,s,-CHOH), 5.03 (1H,d,$J_{4.5}$Hz, $C_6$-H), 5.52 and 5.83 (2H, ABq, J13.5Hz, $CH_2SR$), 6.35(2H,s, $C_2$-$H_2$), and 7.36 (3H,s, thiadiazole methyl protons).

b.
(6R,7R,2′S)-7-[2′-Hydroxy-2′-(thien-2-yl)-acetamido]-3-(5-methyl-1,3,4-thiadiazol-2-yl)-thiomethyl-3-em-4-carboxylic Acid The title compound (30.3mg, 0.625 mmole, 57%) was obtained as a pale-yellow amorphous solid from the corresponding diphenylmethyl ester (67mg, 0.11 mmole) by treatment with trifluoroacetic acid (1ml) and anisole (2ml) in the conventional manner [see Example 8 (b)]$\lambda_{max}$ 271.5nm; τ($Me_2$-SO-$D_6$) 1.25 (1H,d,J9Hz, NH), 2.55 (d. J5Hz, thien-5-yl proton), 2.95 (2H,m,thien-3- and 4-yl protons), 4.30 (1H, dd, J9 and 4.5Hz, $C_7$-H), 4.62 (1H,s,-CHOH), 4.90 (1H,d,J4.5Hz, $C_6$-H), 5.44 and 5.74 (2H, ABq, J13.5Hz, $CH_2SR$), 6.10 (broad singlet, $C_2$-$H_2$) and 7.32 (3H,s, thiadiazole methyl protons).

EXAMPLE 14

Diphenylmethyl (6R,7R,2′R and S)-7-(2′-Hydroxyphenylacetamido)-3-(1-methyltetrazol-5-yl)-thiomethylceph-3-em-4-carboxylate A mixture of diphenylmethyl (6R,7R)-7-isocyano-3-(1-methyltetrazol-5-yl)-thiomethylceph-3-em-4-carboxylate (151mg, 0.3 mmole), benzaldehyde (1ml), and 8N-sulphuric acid (0.019ml, 0.15 mmole) was stirred at +20 to +25° for 15 mins. and then diluted with methylene chloride (50ml). The solution was washed with 3%-aqueous sodium bicarbonate solution (30ml), dried, and then evaporated. The residue was chromatographed on kieselgel G (15g) in methylene chlorideethanol (97:3) to give the title compound as a foam (159mg, 0.094 mmole, 31%); τ($Me_2SO$-$D_6$) 1.20 and 1.29 (total 1H, 2d, J9Hz, NH), 2.60(15H,m,[$C_6H_5$]$_2$CH and $C_6H_5$CH), 3.08 (1H,s, [$C_6H_5$]$_2$CH), 4.20(m, $C_7$-H), 4.84 and 4.90 (total 1H,2d,J4.5Hz, $C_6$-H), 4.86 (1H,s,$C_6H_5$CH), 5.60 and 5.82 (2H, ABq, J13Hz, $CH_2SR$), 6.11 (3H,s, tetrazole methyl protons), 6.24(2H, broad,s, $C_2$-$H_2$).

Preparation of Starting Materials

The following method was used to prepare the 6-formamidopenicillin starting material of Example 1.

i. A mixture of (3S,5R,6R)-6-amino-2,2-dimethylpenam-3-carboxylic acid (6-APA, 2.2056 g., 10.21 mmole), trimethyl chlorosilane (2.615 ml., 20.42 mmole), and triethylamine (2.84 ml., 20.3 mmole) in tetrahydrofuran), (50 ml.) was stirred for 1 hour at +20 to +25° and then cooled to −70°. To this solution at −70° was added a cold (−60 to −70°solution of formic-acetic anhydride [generated by stirring formic acid (470 mg., 10.2 mmole), acetyl chloride (0.726 ml., 10.2 mmole) and triethylamine (1.42 ml., 10.2 mmole) at −60 to −70° in tetrahydrofuran (40 ml.). The solution contained suspended triethylamine hydrochloride] and triethylamine (1.42 ml., 10.2 mmole). The temperature of the mixture was allowed to rise to +20° over ca. 1 hour and the mixture was then filtered. The filtrate and washings were stirred and a solution of sodium 2-ethylhexanoate (2g., 12 mmole) in tetrahydrofuran (2ml.) and ether (18 ml.) was added. The white precipitate was isolated by filtration, washed with ether and dried to give sodium (3S,5R,6R)-6-formamido-2,2-dimethylpenam-3-carboxylate as a white powder (1.6127 g., 6.06 mmole), 59.4%); m.p. 238° to 242° (dec.); [α]$_D$ + 281° ($H_2O$); $\nu_{max}$ 3412 (NH), 1790 (azetidin-2-one), 1677 and 1505 (CONH), 1602 cm.$^{-1}$ ($CO_2^-$); τ 1.28 (1H, d, J 9 Hz, NH), 1.90 (1H, s, HCO), 4.40 to 4.60 (2H, m, $C_5$-H and $C_6$-H), 6.01 (1H, s, $C_3$-H), 8.42 (3H, s) and 8.50 (3H, s) (C[$CH_3$]$_2$). (Found : C, 40.7; H, 4.3; N, 10.3; Na, 8.6; S, 11.7. $C_9H_{11}N_2NaO_4S$ (266.3) requires C, 40.5; H, 4.1; N, 10.5; Na, 8.6; S, 12.0%).

ii. A mixture of sodium (3S,5R,6R)-6-formamido-2,2-dimethylpenam-3-carboxylate (15.0109 g., 56.4 mmole) and p-nitrobenzyl bromide (12.16805 g., 56.3 mmole) in N,N-dimethylformamide (250 ml.) was stirred for 4 hours at +20 to +25°, after which time all the solid had dissolved. The solvent was removed by evaporation and the residual paste was suspended in ethyl acetate (100 ml.) and washed with brine. The aqueous layer was washed with ethyl acetate (150 ml.) and the combined organic layers washed with water (5 × 250 ml.), passed through phase-separating paper and evaporated to a pale-yellow foam. Chromatography on kieselgel G (600 g.) in benzene-ethyl acetate (1:1) gave p-nitrobenzyl (3S,5R,6R)-6-formamido-2,2-dimethylpenam-3-carboxylate which crystallised from ether-ethyl acetate (3:1) as a white solid (8.73 g., 23 mmole, 41%); m.p. 129° to 132°; [α]$_D$ + 190°; $\lambda_{max}$ 262 (ε 10,170); $\nu_{max}$ 3420 (NH), 2880 (HCO), 1788 (azetidin-2-one), 1750 ($CO_2R$), 1695 and 1505 (CONH), 1528 and 1346 (Ar-$NO_2$), 841 cm.$^{-1}$(paradisubstituted aromatic ring); τ1.73, 2.43 (2H, AB-q, J8.5 Hz, p-nitrophenyl), 1.75 (1H, s, HCO), 3.37 (1H, d, J 9 Hz, NH), 4.21 (1H, dd, J 9 and 4.5 Hz, $C_6$-H), 4.42 (1H, d, J 4.5 Hz, $C_5$-H), 4.68 (2H, s, $NO_2C_6H_4CH_2$), 5.46 (1H, s, $C_3$-H), 8.36 (3H, s) and 8.54 (3H, s) (C[$CH_3$]$_2$). (Found : C, 50.5; H, 4.6; N, 11.1; S, 8.5. $C_{16}H_{17}N_3O_6S$ (379.4) requires C, 50.7; H, 4.6; N, 11.1; S, 8.4%).

We claim:
1. A penicillin compound having the formula

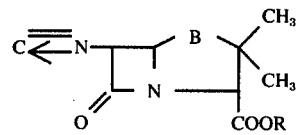

wherein R is a conventional carboxyl blocking group; and B is >S or >S  0.
2. The compound of claim 1 wherein B is >S.
3. The compound of claim 1 which is p-nitrobenzyl (3S,5R,6R and S)-6-isocyano-2,2-dimethylpenam-3-carboxylate.

* * * * *